United States Patent
Olson

(10) Patent No.: US 10,245,048 B2
(45) Date of Patent: *Apr. 2, 2019

(54) SHAPE-FIT GLENOID REAMING SYSTEMS AND METHODS

(71) Applicant: Howmedica Osteonics Corp., Mahwah, NJ (US)

(72) Inventor: Nicholas Olson, Belleville, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/852,047

(22) Filed: Dec. 22, 2017

(65) Prior Publication Data

US 2018/0116683 A1 May 3, 2018

Related U.S. Application Data

(63) Continuation of application No. 15/446,423, filed on Mar. 1, 2017, now Pat. No. 9,877,737, which is a
(Continued)

(51) Int. Cl.
*A61B 17/17* (2006.01)
*A61B 17/88* (2006.01)
(Continued)

(52) U.S. Cl.
CPC ...... *A61B 17/1778* (2016.11); *A61B 17/1684* (2013.01); *A61B 17/1703* (2013.01);
(Continued)

(58) Field of Classification Search
CPC . A61B 17/17; A61B 17/1735; A61B 17/1739; A61B 17/16; A61B 17/1684
See application file for complete search history.

(56) References Cited

U.S. PATENT DOCUMENTS 6,235,034 B1 5/2001 Bray
8,337,503 B2 12/2012 Lian
(Continued)

FOREIGN PATENT DOCUMENTS

WO 2013060851 A1 5/2013

*Primary Examiner* — Christopher Beccia
(74) *Attorney, Agent, or Firm* — Lerner, David, Littenberg, Krumholz & Mentlik, LLP

(57) ABSTRACT

Disclosed herein are systems and methods for securing a glenoid baseplate to a resected glenoid cavity in a preoperatively planned position. Image information obtained from the glenoid cavity and surrounding scapula is analyzed to determine the location of optimal bone stock. A guide is designed based on the image information, the guide having a patient specific contact surface that contacts a surface of the bone in a preoperatively planned position. The guide is designed to have a cannulated portion including a specific length. A marking pin having at least one reference feature is drilled into the glenoid cavity. The length of the cannulated portion of the guide is based on a location of the at least one reference feature on an outer surface of the marking pin. A cannulated reamer guided by the marking pin is then used to resect the glenoid cavity until a stop surface of the cannulated reamer contacts an end of the marking pin.

20 Claims, 18 Drawing Sheets

Related U.S. Application Data continuation of application No. 14/218,174, filed on Mar. 18, 2014, now Pat. No. 9,615,839.

(51) Int. Cl.
  *A61B 17/16* (2006.01)
  *A61F 2/40* (2006.01)
  *A61B 90/00* (2016.01)

(52) U.S. Cl.
  CPC ...... *A61B 17/1739* (2013.01); *A61B 17/8897* (2013.01); *A61B 2090/062* (2016.02); *A61F 2/4081* (2013.01)

(56) References Cited

U.S. PATENT DOCUMENTS

| | | |
|---|---|---|
| 8,523,862 B2 | 9/2013 | Murashko, Jr. |
| 9,615,839 B2 | 4/2017 | Olson |
| 2006/0116679 A1 | 6/2006 | Lutz et al. |
| 2010/0217399 A1 | 8/2010 | Groh |
| 2012/0010619 A1* | 1/2012 | Barsoum ............ A61B 17/8897 606/79 |
| 2012/0141034 A1 | 6/2012 | Iannotti et al. |
| 2012/0289965 A1 | 11/2012 | Gelaude et al. |
| 2013/0110116 A1* | 5/2013 | Kehres ............... A61B 17/1739 606/96 |
| 2013/0110470 A1 | 5/2013 | Vanasse et al. |
| 2013/0150973 A1 | 6/2013 | Splieth et al. |
| 2013/0245631 A1* | 9/2013 | Bettenga ............ A61B 17/1666 606/91 |
| 2013/0267958 A1 | 10/2013 | Iannotti et al. |
| 2014/0012266 A1* | 1/2014 | Bonin, Jr. .............. A61B 17/15 606/88 |

\* cited by examiner

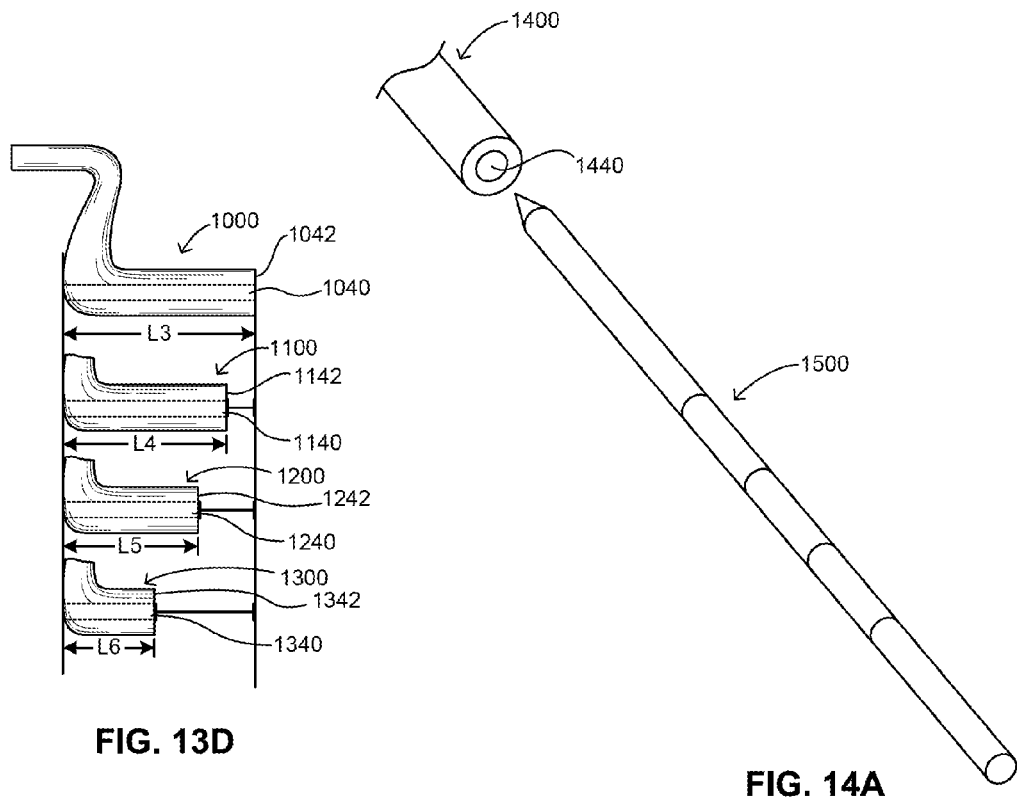
FIG. 13D
FIG. 14A
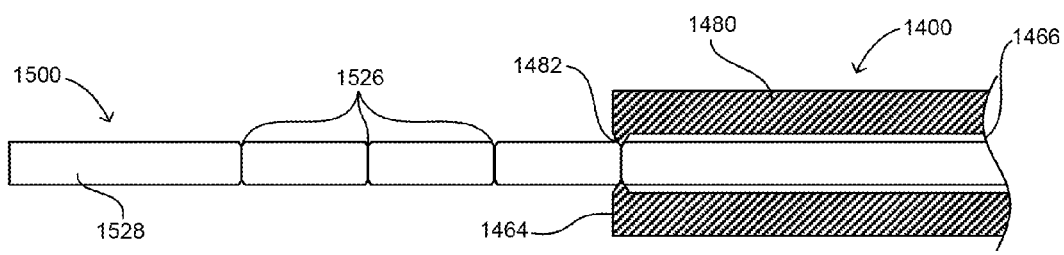
FIG. 14B

SHAPE-FIT GLENOID REAMING SYSTEMS AND METHODS

CROSS-REFERENCE TO RELATED APPLICATIONS

The present application is a continuation of U.S. application Ser. No. 15/446,423, filed on Mar. 1, 2017 which is a continuation of U.S. application Ser. No. 14/218,174, now U.S. Pat. No. 9,615,839, filed on Mar. 18, 2014, the disclosures of which is incorporated herein by reference.

FIELD OF THE INVENTION

The present invention relates to the use of patient-specific guides in shoulder arthroplasty procedures, and in particular relates to the use of first and second patient-specific guides during such procedures to ensure that components of a shoulder arthroplasty system are fixated with respect to bone in a preoperatively planned position and orientation.

BACKGROUND OF THE INVENTION

Joint replacement procedures are used to repair damaged joints. During a joint replacement procedure the joint is preferably aligned, bone or bones of the joint may be resected, and a prosthesis may be implanted on the resected bone. Joint replacement procedures may be performed on the knee, hip, shoulder or elbow joints, for example. Accuracy of joint alignment and bone resection is crucial in a joint replacement procedure. A small misalignment may result in soft tissue or ligament imbalance and consequent failure of the joint replacement procedure. Provision of patient specific or customized cutting guides and prostheses has been used to attempt to improve the outcome of joint replacement procedures.

Preoperative planning is used to prepare a surgical plan based on the scan data or to determine what instruments or prosthetic components should be used to achieve a desired surgical result. Preoperative planning is also used to design such patient-specific guides and prostheses for use in joint replacement procedures. Prior to the surgical procedure, scan data associated with a joint of the patient is generally obtained, a three-dimensional model of the joint based on the scan data is prepared, and guides and/or prostheses based on the model are designed. Once the guides and/or prostheses are designed, information regarding manufacture of these components may be sent to additive manufacturing equipment for manufacture, for example.

Patient-specific guides generally include an inner guide surface designed to mate with a joint surface of the patient such that the guide and joint surface are in a nesting relationship to one another. Accordingly, such guides may mate or "lock" onto the articular surface of the joint in a unique position determined in a final surgical plan. Apertures in the guide are generally designed to locate a guide member or guide a resection device. The guides are preferably designed with such apertures in a preoperatively planned position in order to achieve a desired bone resection such that a prosthesis can be placed in a desired position and orientation.

In tradition and reverse shoulder arthroplasty procedures it is important to accurately locate a prosthesis for attachment to the scapula. In these procedures, fixation screws are used to secure a glenoid cup or baseplate for glenosphere, for example, to the scapula. In order for the cup or baseplate to be sufficiently secured to endure loads during physical therapy and use post surgery, the fixation screws generally need to be fixated to healthy bone stock. There exists a need for locating these prostheses along with fixation screws thereof in a preoperatively planned position and orientation with respect to the native bone stock.

BRIEF SUMMARY OF THE INVENTION

A first aspect of the present invention is a method for attaching a baseplate to a glenoid in a shoulder arthroplasty procedure. The method includes scanning the patient anatomy, namely the shoulder joint including at least the glenoid and scapula. The scan is analyzed to determine optimal prosthesis placement and fixation based on available bone stock. After analyzing prosthesis placement and fixation, first and second guides are designed to ensure that such placement and fixation is reproducible intraoperatively. The first guide is configured to directly interface with the bone for optimal baseplate placement and the second guide directly interfaces with the baseplate for optimal screw fixation.

The method may include contacting the glenoid with a first guide having a central borehole and a first reference marker and placing a pilot wire through the central borehole and into the glenoid. Further, the method may include orienting the baseplate with respect to the glenoid by inserting the pilot wire through a central screw hole of the baseplate and aligning a marker on the baseplate with respect to the first reference marker of the first guide and then attaching a second guide to the baseplate such that at least one borehole of the second guide is aligned to at least one peripheral screw hole of the baseplate.

A second aspect of the present invention is a method of attaching a baseplate to a glenoid in a shoulder arthroplasty procedure comprising using a first guide to create a first reference and a second reference with respect to the glenoid, orienting the baseplate with respect to the glenoid using the first and second references, fixing the baseplate to the glenoid with a central screw, and attaching a second guide to the baseplate such that at least one borehole of the second guide is aligned to at least one peripheral screw hole of the baseplate.

In one embodiment of this second aspect, the first guide has a patient specific contact surface that contacts the glenoid such that the first guide engages the glenoid in a preoperatively planned position. The patient specific contact surface of the first guide is preferably created using image information obtained from scanning the glenoid.

In another embodiment of this second aspect, the method further comprises creating the first reference by inserting a pilot wire through a central borehole in the first guide and at least partially into the glenoid and creating the second reference by marking the glenoid using a first reference marker on the first guide. The second reference mark may be a notch located on an outer periphery of the first guide.

In yet another embodiment of this second aspect, the central borehole of the first guide includes a central axis having a first trajectory with respect to the glenoid when the first guide is engaged to the glenoid.

In still yet another embodiment of this second aspect, orienting the baseplate with respect to the glenoid using the second reference includes aligning a marker on the baseplate with respect to the notch of the first guide by rotating the baseplate until the marker of the baseplate is adjacent the notch of the first guide.

In still yet another embodiment of this second aspect, the baseplate includes four peripheral screw holes and the second guide includes four boreholes, wherein attaching the second guide to the baseplate includes aligning each of the four boreholes of the second guide to one of the four peripheral screw holes of the baseplate. Each of the four boreholes of the second guide and each of the four peripheral screw holes preferably includes a trajectory and the trajectories of at least one of four boreholes and at least one of the four corresponding peripheral screw holes is not coaxial with one another.

Third aspect of the present invention is a method of orienting peripheral screws through peripheral screws holes of a baseplate and into a glenoid comprising scanning the glenoid to determine desirable bone stock thereof, determining a first angle a first peripheral screw should be inserted through a first peripheral screw hole of the baseplate and into glenoid when the baseplate is engaged to the glenoid in a desired position and orientation, using a first guide to create a first reference and a second references with respect to the glenoid, orienting the baseplate with respect to the glenoid using the first and second references, attaching a second guide to the baseplate such that at least one peripheral screw hole of the second guide is aligned to at least one peripheral screw hole of the baseplate, and fixing the baseplate to the glenoid with at least one peripheral screw inserted through the at least one peripheral screw hole of the second guide and the at least one peripheral screw hole of the baseplate and into the glenoid.

In one embodiment of this third aspect, the at least one peripheral screw hole of the second guide and the baseplate have a central longitudinal axis and when the at least one peripheral screw hole of the second guide is aligned to at least one peripheral screw hole of the baseplate, the central longitudinal axes are angled with respect to one another.

In yet another embodiment of this third aspect, the first reference is created by inserting a pilot wire through a central borehole in the first guide and at least partially into the glenoid and the second reference is created by marking the glenoid using a first reference marker on the first guide. The second reference marker is preferably a notch located on an outer periphery of the first guide.

In still yet another embodiment of this third aspect, the central borehole of the first guide includes a central axis having a first trajectory with respect to the glenoid when the first guide is engaged to the glenoid.

In still yet another embodiment of this third aspect, orienting the baseplate with respect to the glenoid using the second reference includes aligning a marker on the baseplate with respect to the notch of the first guide by rotating the baseplate until the marker of the baseplate is adjacent the notch of the first guide.

A fourth aspect of the present invention is a system for resecting a preoperatively planned depth into bone comprising a guide having a patient specific contact surface that contacts a surface of the bone in a preoperatively planned position, the guide having a cannulated portion including a length; and a marking pin having first and second ends, the first end adapted to be drilled into the bone, the marking pin having at least one reference feature on an outer surface thereof, wherein the length of the cannulated portion of the guide is based on a location of the at least one reference feature on the outer surface of the marking pin.

A fifth aspect of the present invention is a method of resecting a preoperatively planned depth into bone comprising contacting a surface of the bone in a preoperatively planned position with a guide having a patient specific contact surface, the guide having a cannulated portion including a length; inserting a first end of a marking pin into the cannulated portion of the guide and into contact with the surface of the bone, the marking pin having at least one reference feature on an outer surface thereof; and drilling at least a portion of the marking pin into the bone until the at least one reference feature on the outer surface of the marking pin lies adjacent a receiving end of the cannulated portion of the guide.

BRIEF DESCRIPTION OF THE DRAWINGS

The present invention will be better understood on reading the following detailed description of non-limiting embodiments thereof, and on examining the accompanying drawings, in which:

FIG. 13D is a plan view of cannulated portions of four patient-specific guides each having a different length.

FIG. 14A is an exploded perspective view of one embodiment of guidewire gauge and a cannulated portion of a patient-specific guide.

FIG. 14B is partial cross-sectional view of a portion of a guidewire gauge housed within a cannulated portion of one embodiment of a patient-specific guide having grasping features on an inner surface of the cannulated portion.

DETAILED DESCRIPTION

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Figure 1:
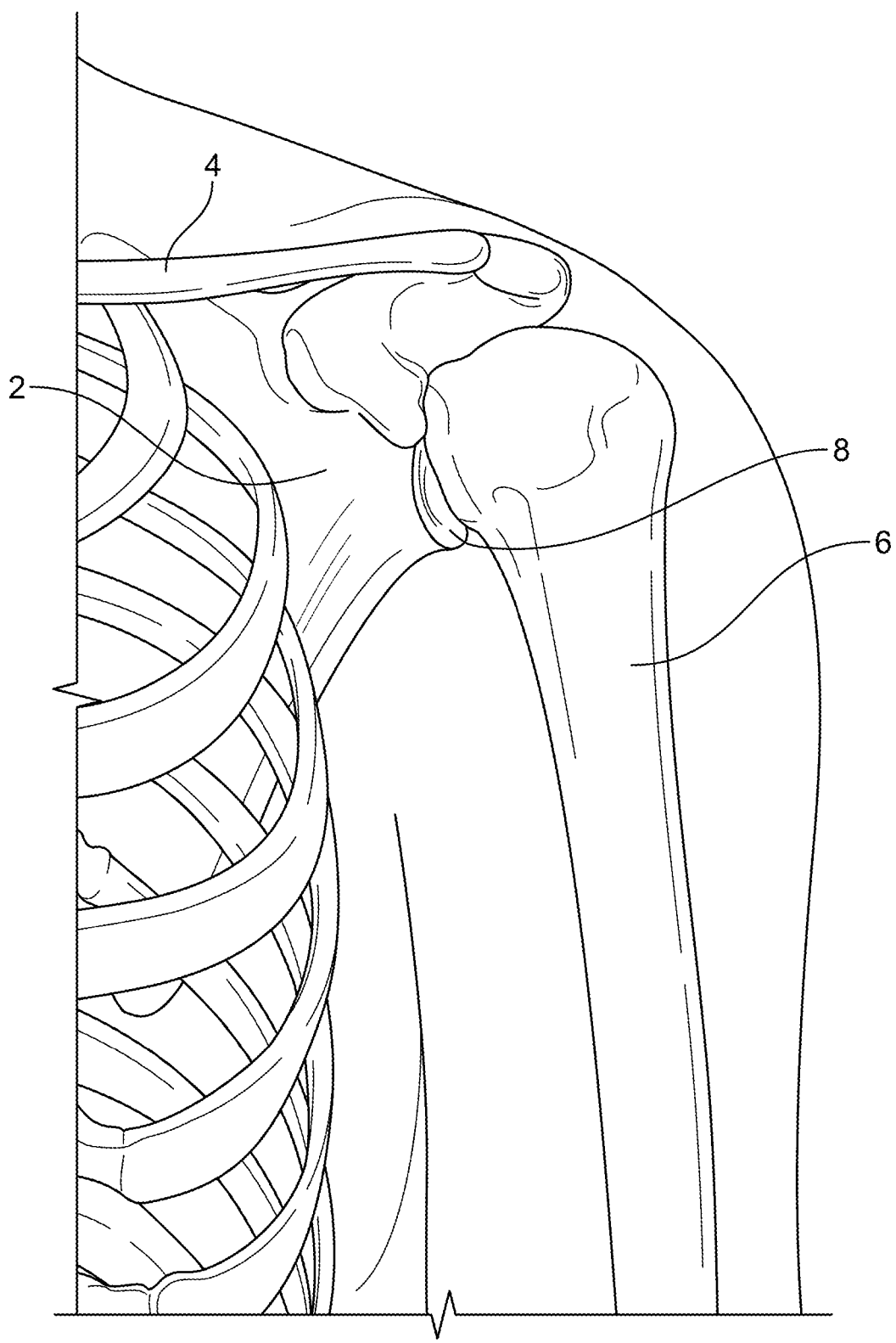
FIG. 1 is an anterior view of general shoulder anatomy.
Figure 2:
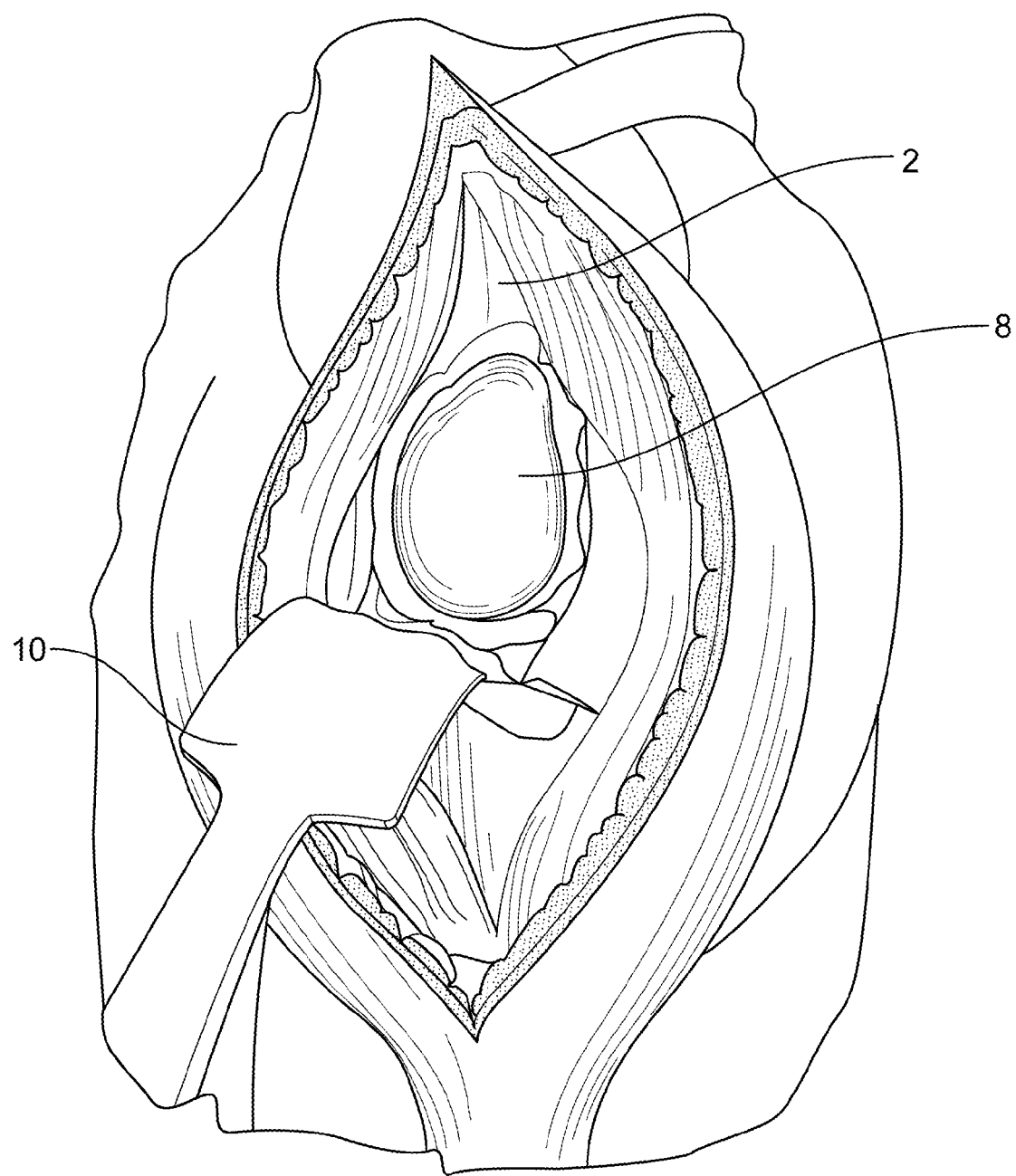
FIG. 2 is a lateral view of one embodiment of a surgical approach to the glenoid.

FIG. 1 is an anterior view of shoulder anatomy, including a scapula 2, clavicle 4, humerus 6, and glenoid 8. FIG. 2 is a lateral view of a surgical approach to glenoid 8 in which a surgical retractor 10 is shown moving soft tissues from the surgical site to expose glenoid 8. In shoulder arthroplasty procedure it is essential that a glenoid baseplate be positioned accurately on a glenoid prior to coupling the baseplate to other components of a shoulders system such as a glenosphere and humeral stem, for example. The present invention includes preoperatively planning the position and orientation of central and peripheral screws that are used to fix a baseplate 200 with respect to a glenoid 8 in a shoulder arthroplasty procedure by analyzing available bone stock. A first patient-specific guide 100 is designed to directly interface with glenoid 8 for optimal baseplate 200 placement and a second patient-specific guide 300 is designed to directly interface with baseplate 200 for optimal peripheral screw fixation.

Figure 3B:
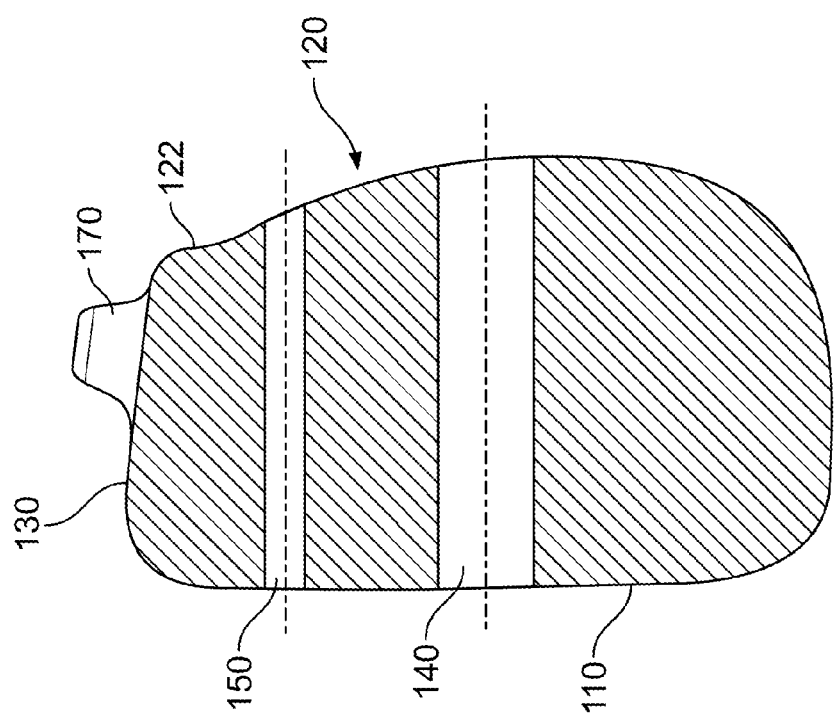
FIG. 3B is a side cross-sectional plan view of the guide shown in FIG. 3A taken along line 3B-3B.
Figure 3A:
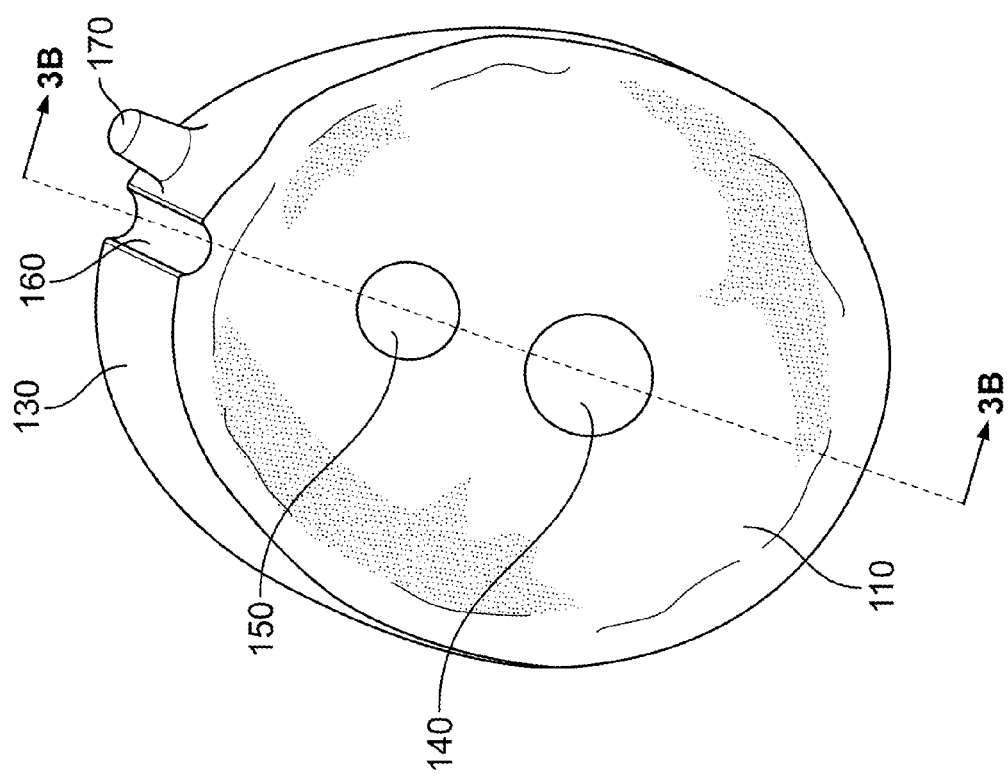
FIG. 3A is a perspective view of one embodiment of a patient-specific guide for engaging an unresected glenoid.

First guide 100 shown in FIGS. 3A and 3B includes an outer surface 110, a patient-specific inner contact surface 120, and a side surface 130 located between outer and inner surfaces 110, 120. First guide 100 includes a central borehole 140 therethrough. Central borehole 140 may be considered as a first reference means as it is used to mark the glenoid in a preoperatively planned position and trajectory. First guide 100 may further include a second borehole 150 therethrough, a notch 160 located as a recess in side surface 130, and/or a mechanical or visual indicator 160 on or in guide 100. Each of second borehole 150, notch 160, and indicator 170 may be considered as a second reference means used to further mark the glenoid to aid in placement of glenoid baseplate 200 in a preoperatively planned position and orientation. Each of these second reference features may be used to mark the glenoid for rotational alignment of glenoid baseplate 200.

Patient-specific inner contact surface 120 of first guide 100 is designed to contact glenoid 8 in a preoperatively planned position. Design of the guide includes scanning the shoulder joint using magnetic resonance imaging ("MRI") or computed tomography ("CT"), for example. A virtual model 8 of glenoid may be created such that it may be shown on a graphics user interface ("GUI") such as a computer screen. Contact surface 120 is designed as a negative of at least a portion of glenoid 8 and may include an anatomic reference feature 122 such that the first guide 100 may be dialed into its preoperatively planned position. The purpose of dialing in a patient-specific guide such a first guide 100 is that the guide is stably oriented with respect to the surface that it is designed to contact in all six degrees of freedom. Design of anatomic reference features, such as feature 122 in guide 100 for aiding in proper patient-specific guide orientation with respect to a joint surface it is designed to engage is disclosed, for example, in U.S. Pat. Pub. No. 2011/0313424 titled "Patient-Specific Total Hip Arthroplasty," the disclosure of which is incorporated by reference herein in its entirety.

Figure 4A:
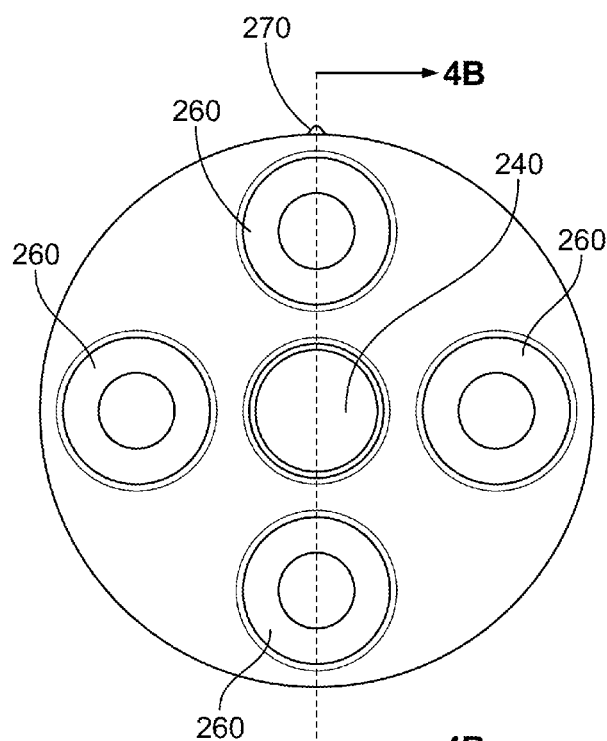
FIG. 4A is a front plan view of one embodiment of a glenoid baseplate for engaging a resected glenoid.
Figure 4B:
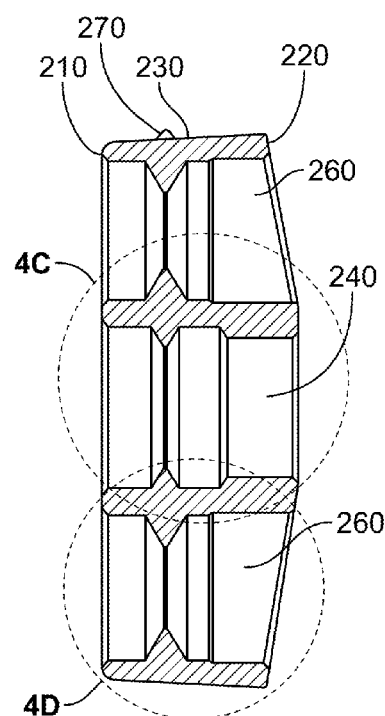
FIG. 4B is a side cross-sectional plan view of the baseplate shown in FIG. 4A.
Figure 4C:
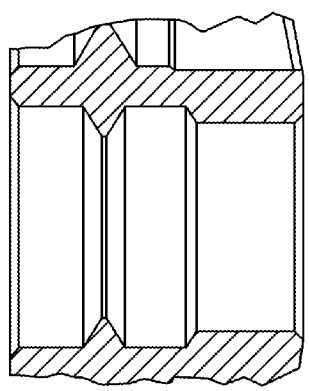
FIG. 4C is a detail view of a central screw hole of the baseplate shown in FIG. 4B taken along line 4B-4B.
Figure 4D:
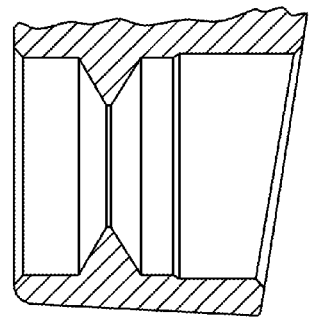
FIG. 4D is a detail view of a peripheral screw hole of the baseplate shown in FIG. 4B taken along line 4B-4B.

Baseplate 200 is shown in FIGS. 4A-D and includes an outer surface 210, an inner contact surface 220, and a side surface 230 located between outer and inner surfaces 210, 220. Baseplate 200 includes a central borehole 240 and a plurality of lateral boreholes 260 therethrough. Lateral boreholes 260 are located adjacent a periphery of baseplate 200 defining side surface 130. FIGS. 4C and 4D are detail views of the structure of central borehole 240 and a lateral borehole 260, respectively. As shown in these figures, inner contact surface 220 is generally parallel to outer surface 210 adjacent to central borehole 240 while inner contact surface 220 is angled with respect to outer contact 210 adjacent lateral borehole 260. An example of baseplate 200 including borehole 240 and lateral boreholes 260 is disclosed in U.S. Pat. Pub. No. 2013/0150973 titled "Reverse Shoulder Baseplate with Alignment Guide for Glenosphere," the disclosure of which is incorporated by reference herein in its entirety.

Figure 4E:
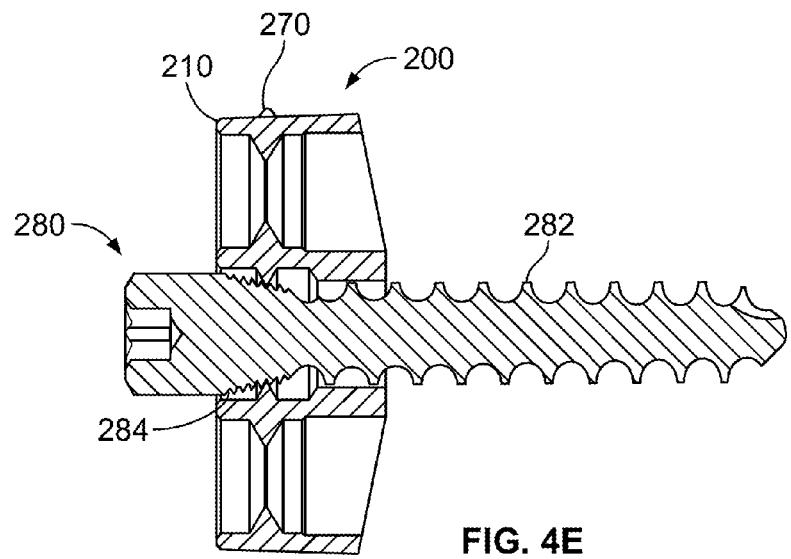
FIG. 4E is a central screw coupled to a central screw hole of the baseplate shown in FIG. 4B.

A central screw 280 as shown in FIG. 4E is received in the central borehole 240 of baseplate 200 such that a head 281 of screw 280 protrudes outwardly from outer surface 210 of baseplate 200. The present invention may include various embodiments of a central screw having a threaded shaft 282 and a threaded neck 284, which can generate a compression force along the length of the screw when inserted into a bone. Central screw 280 of the present invention may create a first compression rate when a shaft and a distal end of the screw are engaged with scapula bone, for example, and a second compression rate when the shaft and a proximal end of the screw are engaged with scapula bone. The second compression rate may be less than the first compression rate, for example. Such central screws are shown and described in U.S. Ser. No. 13/803,615, titled "Compression Screw With Variable Pitch Thread," filed Mar. 14, 2013, the disclosure of which is hereby incorporated by references herein in its entirety.

Figure 5A:
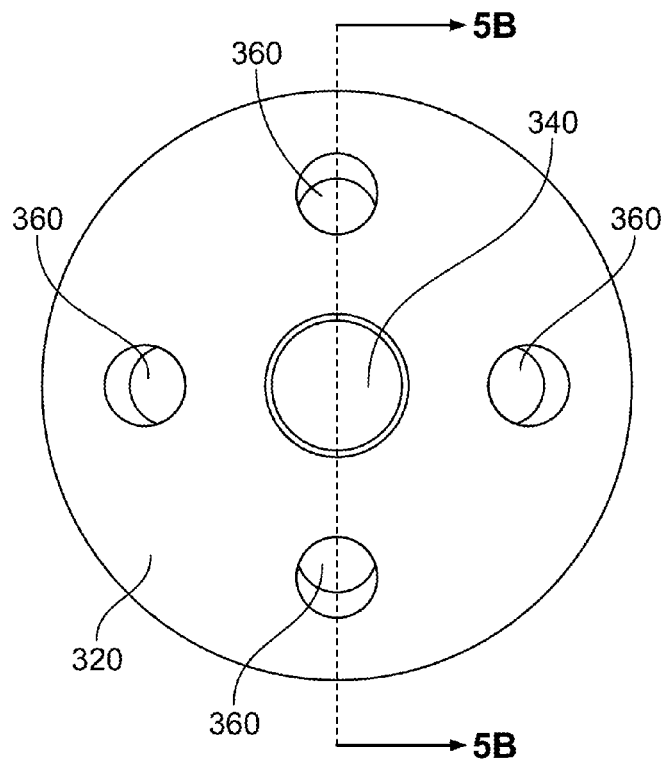
FIG. 5A is a front plan view one embodiment of a patient-specific guide for engaging a glenoid baseplate.
Figure 5B:
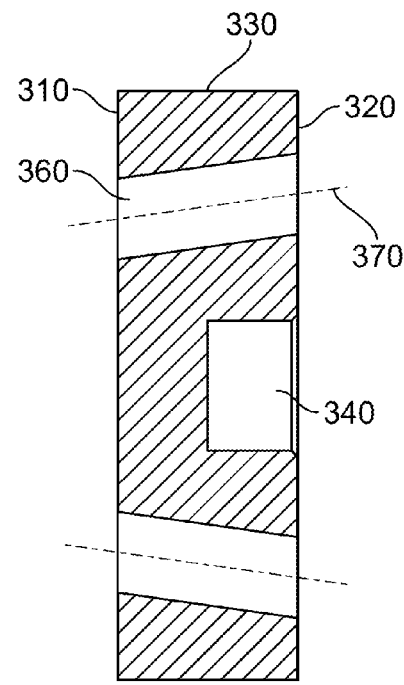
FIG. 5B is a side cross-sectional plan view of the guide shown in FIG. 5A taken along line 5B-5B.

Second patient-specific guide 300 shown in FIGS. 5A and 5B includes an outer surface 310, an inner contact surface 320, and a side surface 330 located between outer and inner surfaces 310, 320. Guide 300 includes a central recess 340 located in inner contact surface 320 for receiving head 281 of screw 280 protruding outwardly from outer surface 210 of baseplate 200. Guide 300 further includes a plurality of lateral or peripheral boreholes 360. Lateral boreholes 360 are located adjacent a periphery of baseplate 200 defining side surface 330. Each of lateral boreholes 360 defines a trajectory defined by an angle between a central axis 370 thereof and inner contact surface 320. Each of lateral boreholes 360 may include a unique trajectory. For example, a first lateral borehole 360 may have a trajectory of 60° while a second lateral borehole 75°. Guide 300 preferably has four lateral boreholes 360 each with a unique optimal trajectory based on preoperative scans taken of the patient's scapula. The trajectories are designed such that when guide 300 is coupled to baseplate 200, the boreholes 260 guide peripheral screws into the lateral boreholes 260 of baseplate 200 and into the glenoid cavity and surrounding scapula at a predefined trajectory based on optimal bone stock. Guide 300 may further include a mechanical or visual indicator 370 used as a reference feature for ensuring accurate coupling of guide 300 to baseplate 200 including accurate rotational alignment of guide 300 with respect to baseplate 200.

One method of the present invention includes preparing the glenoid by targeting the center of the glenoid using a first patient-specific guide having a centering guide hole is used to drill a centering hole. A guide-wire or guide pin is placed into the centering hole and a cannulated reamer is placed over the guidewire to guide reaming of the glenoid face progressively until subchondral bone is thoroughly exposed. A glenoid baseplate is attached to the reamed glenoid face in a desired location. A second patient-specific guide having a plurality of lateral boreholes each having a designed trajectory is attached to the glenoid baseplate. The lateral boreholes are used to guide the trajectory of peripheral screws through the baseplate and into the prepared glenoid.

Figure 6:
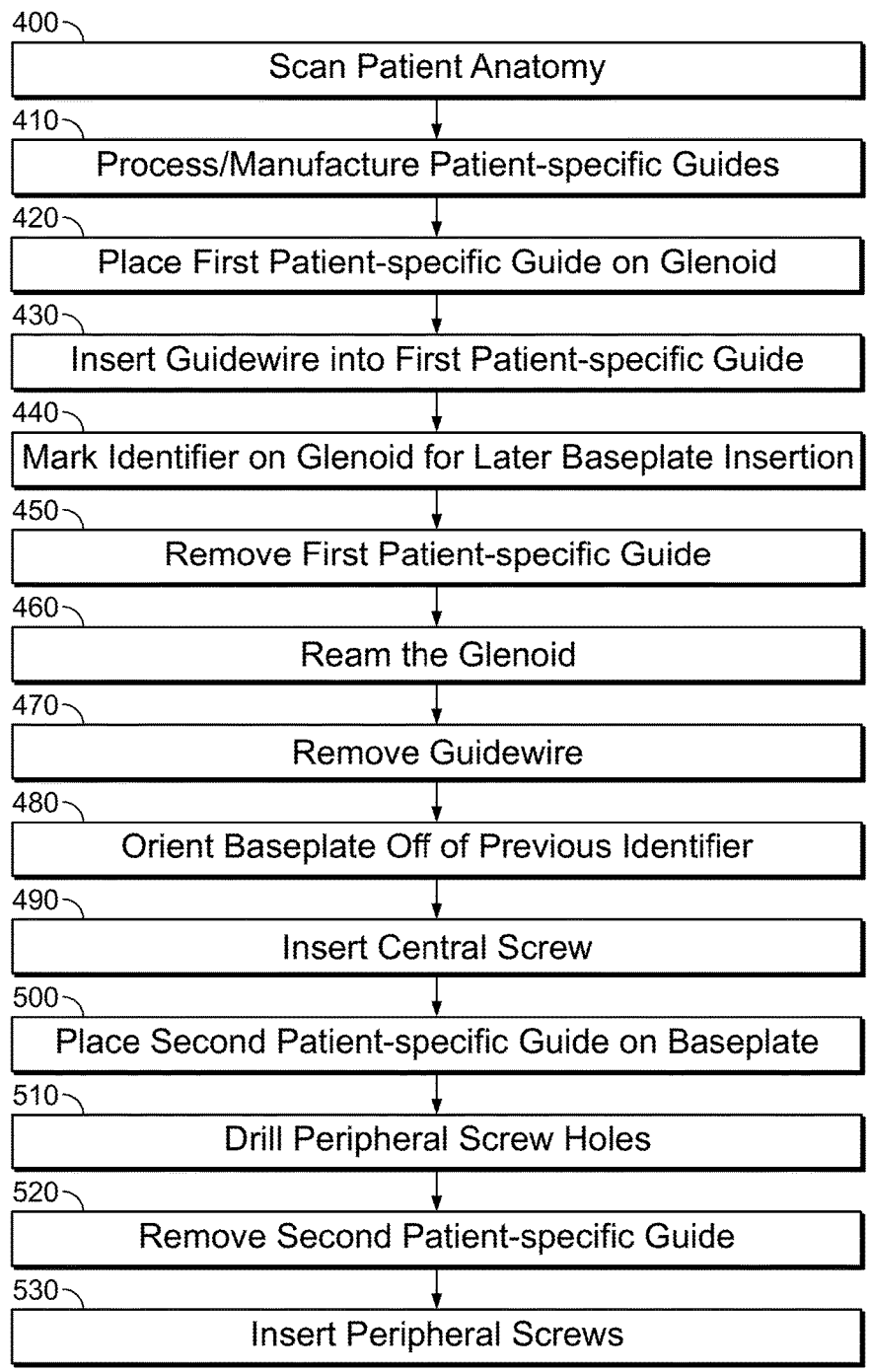
FIG. 6 is a flowchart of one embodiment of a method of the present invention.

FIG. 6 is a flowchart of one embodiment of a method of the present invention. In a first step 400 a patient's anatomy is scanned preferably including the glenoid cavity and surround scapula. In step 410, based on the image information obtained from the scan of the patient's anatomy, first and second patient-specific guides are designed. The design of the first and second guides takes into account the structure of a glenoid baseplate, namely the outer and inner surfaces and thickness thereof as well as the location and orientation of central and peripheral screw holes thereof. In designing the guides, models of the glenoid baseplate and patient anatomy may be made and shown on a GUI such that a designer can design the first and second guides appropriately. Based on a desired location and orientation of the baseplate with respect to the resected glenoid, the patient-specific contact surfaces as well as the location and orientation of reference markers and central and peripheral boreholes can be designed. After the first and second guides are designed, each is manufactured for use intraoperatively.

In a subsequent step 420, the first patient-specific guide is placed in a preoperatively planned position on the unresected glenoid. In a subsequent step 430, a guidewire is inserted through a central borehole of the first guide and into the bone of the glenoid. The guidewire may be a guidewire gauge having reference markings to indicate the depth the guidewire gauge has been inserted into the glenoid and preferably into cortical bone. In a subsequent step 440, a reference guide is used to mark the glenoid for later baseplate insertion. In a further step 450, the first guide is removed and in step 460, the glenoid is reamed to a desired depth using the guidewire gauge. In a further step 470, the guidewire gauge is removed and in step 480 the baseplate is oriented off of previous reference mark or identifier made in previous step 440. In yet a subsequent step 490, a central screw is inserted through a central screw hole of the baseplate and into the resected glenoid to initially fix the baseplate with respect to the resected glenoid. In yet still a subsequent step 500, a second patient-specific guide is coupled to the baseplate and oriented such that peripheral boreholes of the second guide are aligned in a preoperatively planned position with respect to peripheral screw holes of the baseplate. Once the peripheral boreholes of the second guide are aligned with the peripheral screw holes of the baseplate, in step 510 peripheral screw holes are drilled through the baseplate and into the resected glenoid. In a subsequent step 520, the second guide may be removed and in step 530 peripheral screws are inserted into the peripheral screw holes of the baseplate in a trajectory the peripheral screw holes were drilled using the second guide in step 510.

Figure 7A:
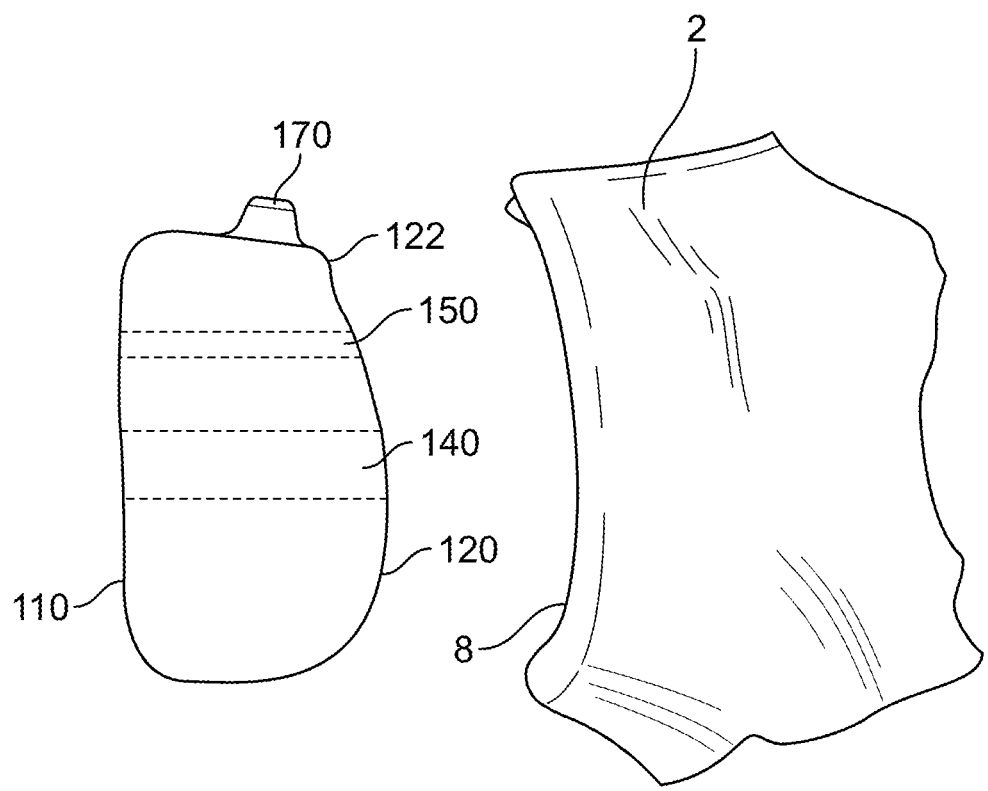
FIG. 7A is an anterior view of the scapula of one embodiment of a patient-specific guide used in marking the glenoid for locating a glenoid baseplate in a preoperatively planned position and orientation.
Figure 7B:
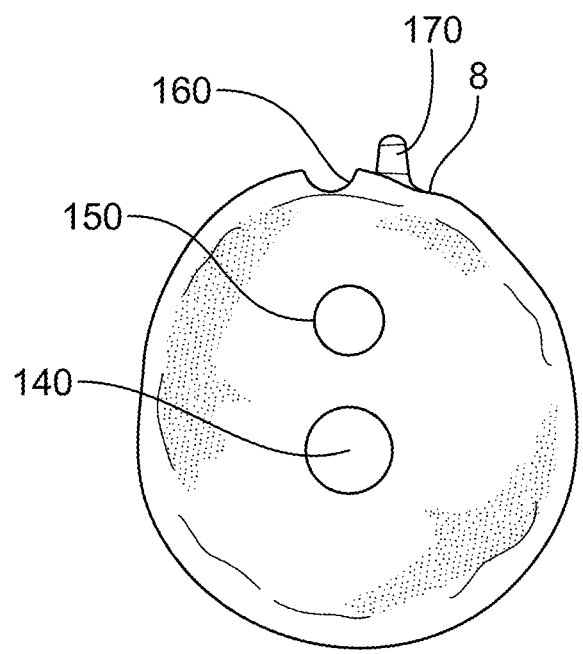
FIG. 7B is a lateral view of the guide shown in FIG. 7B engaged to the glenoid.

FIGS. 7A and 7B refer to steps 420-450 described above. FIG. 7A is an anterior view of the scapula of one embodiment of first patient-specific guide 100 used in marking the glenoid for locating a glenoid baseplate in a preoperatively planned position and orientation with FIG. 7B showing a lateral view of guide 100 engaged to the glenoid. The first guide 100 has at least two functions, namely fixing the location for pilot wire insertion and acting as a marker to orient baseplate 200. With respect to the first function, the geometry of guide 100 ensures that it can only be placed on the glenoid of the patient in one orientation. Because the guide has a patient-specific contact surface 120, the guide 100 can be dialed in until it is oriented in the preoperatively planned orientation. Once the guide is placed in its proper orientation, the surgeon may insert a guidewire through guide hole 140 and into the bone. With respect to the second function, once the guidewire is inserted, the surgeon will preferably use a unique identifier or indicator 170 on guide 100 to note which direction is superior. This may be achieved with a surgical pen to mark orientation, a tab that points to native anatomy, or by any other unique identifier, for example. This marker will later be aligned with a feature 270 on baseplate 200 to ensure baseplate 200 is oriented in a preoperatively planned orientation.

Figure 8A:
FIG. 8A is one embodiment of a guidewire gauge for guiding reaming depth of a glenoid.

FIGS. 8A-8E refer to step 460 described above. FIG. 8A is one embodiment of a guidewire gauge 600 for guiding reaming depth of a glenoid. Gauge 600 includes a proximal portion 610, a distal portion 620 and a plurality of depth markings along the length of the gauge adjacent the proximal and distal portions. During first step 400, in which a patient's anatomy is scanned, and the subsequent step 410, in which first and second patient-specific guides 100, 300 are designed, software will also assess cortical thickness of glenoid 8, namely the glenoid face. Upon analysis of the cortical thickness, a recommended reaming depth that optimizes cortical thickness for a given baseplate curvature will be given. This allows for maximum placement and inhibits over-reaming the glenoid in improper version.

Figure 8B:
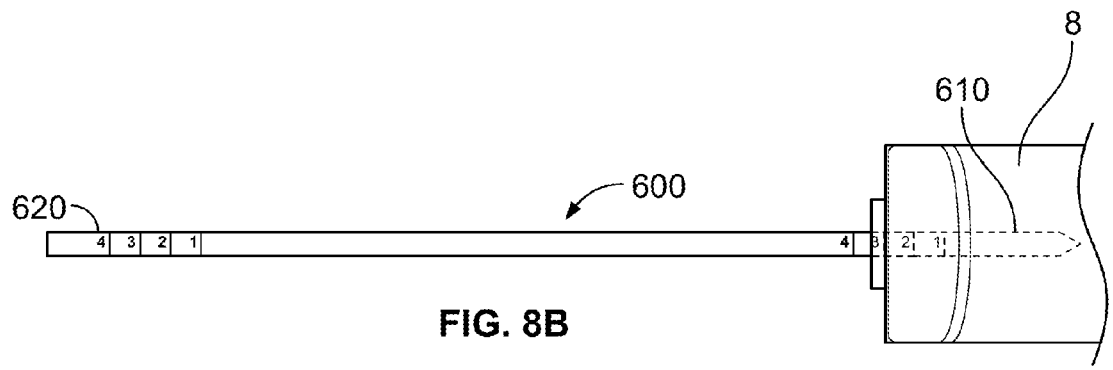
FIG. 8B is one embodiment of the guidewire gauge shown in FIG. 8A coupled to a guide engaged to the glenoid in which an end of the guidewire gauge is located a desired distance into the glenoid cavity.
Figure 8C:
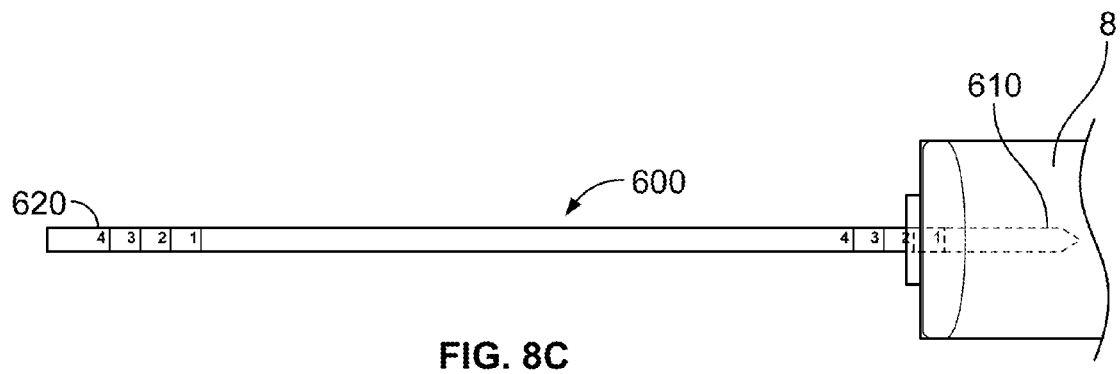
FIG. 8C is one embodiment of the guidewire gauge shown in FIG. 8A coupled to another embodiment of a guide engaged to the glenoid in which an end of the guidewire gauge is located a desired distance into the glenoid cavity.

FIGS. 8B and 8C show the guidewire gauge shown in FIG. 8A coupled to guides having a greater and lesser thickness, respectively. As shown in FIG. 8B, a guide having a greater thickness contacts glenoid 8 while at least a portion of proximal portion 610 of gauge 600 is located adjacent cortical bone of glenoid 8. Gauge 600 is inserted into cortical bone until a depth "3" is adjacent an outer surface of the guide. As shown in FIG. 8C, a guide having a lesser thickness contacts glenoid 8 while at least a portion of proximal portion 610 of gauge 600 is located adjacent cortical bone of glenoid 8. Gauge 600 is inserted into cortical bone until a depth "2" is adjacent an outer surface of the guide.

Figure 8D:
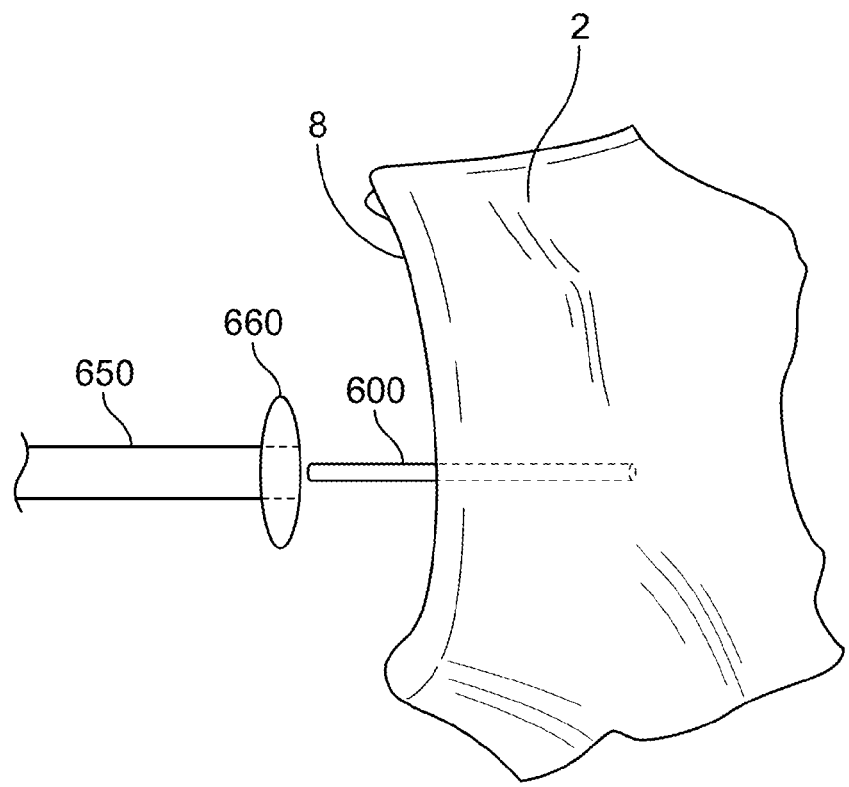
FIG. 8D is an exploded view of the scapula of FIG. 7A with a guidewire gauge located in a marked position and a cannulated instrument for preparing the glenoid.
Figure 8E:
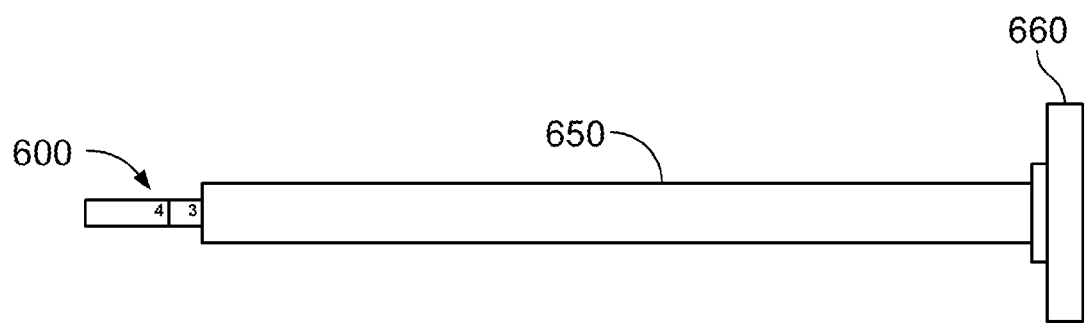
FIG. 8E shows one embodiment of a cannulated instrument coupled to the guidewire gauge of FIG. 8A.
Figure 9:
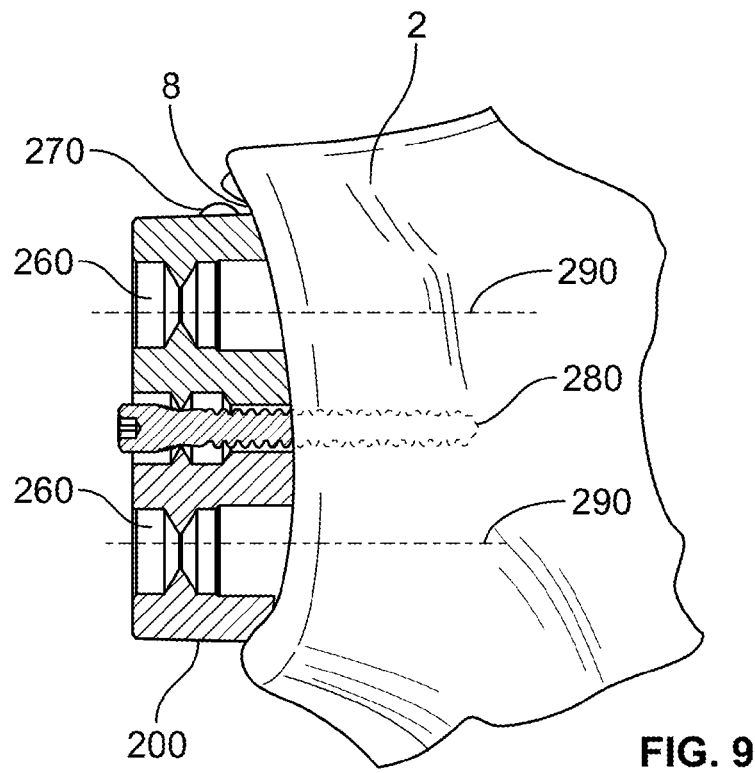
FIG. 9 depicts the scapula of FIG. 3 with one embodiment of a glenoid baseplate secured thereto via a central screw.
Figure 10:
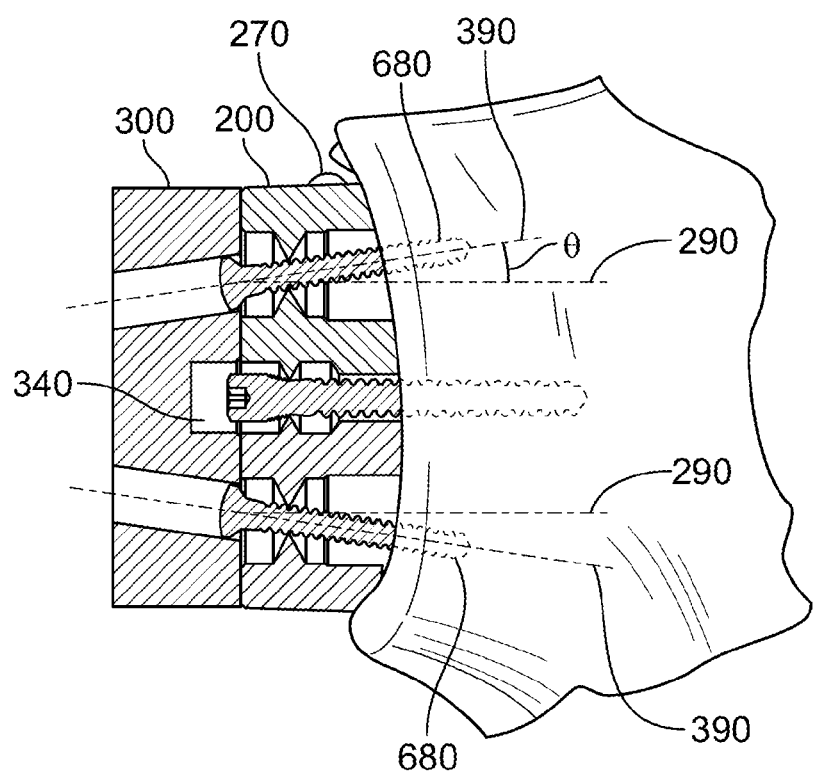
FIG. 10 depicts a patient-specific guide engaged to the glenoid baseplate of FIG. 9B guiding peripheral screws into the baseplate and into the resected glenoid at a preoperatively planned trajectory.

FIG. 8D is an exploded view of the scapula of FIG. 7A with a guidewire gauge 620 located in a marked position and a cannulated instrument 650 having a reamer head portion 660 for preparing the glenoid. FIG. 8E shows cannulated instrument 650 coupled to gauge 600 at depth "3" located at distal portion 620 of gauge 600. Because cannulated instrument 650 covers gauge 600 at proximal portion 610 thereof, the depth markings located at distal portion 620 correlate to the depth makings located at proximal portion 610 such that the user can visualize the reaming depth during glenoid reaming FIGS. 9-10 refer to steps 480-530 described above. FIG. 9 depicts the scapula of FIG. 3 having baseplate 200 secured thereto via central screw 280. FIG. 10 shows patient-specific guide 300 engaged to baseplate 200 of FIG. 9B guiding peripheral screws 680 into baseplate 200 and into the resected glenoid 8 at a preoperatively planned trajectory. Guide 300 functions to align two to four peripheral screws. With respect to this function, guide 300 aligns with baseplate 200 and angles a drill to the optimal trajectory for peripheral screws 680. A surgeon preferably drills through guide 300, through baseplate 200, and into the glenoid 8 for lateral peripheral screw 680 insertion. As shown in FIGS. 9-10, lateral boreholes 260 of baseplate 200 each have a central axis 290 while peripheral screw holes 360 of guide 300 each have a central axis 390. An angle ⊖ is defined by the angle between central axis 290 and central axis 390 of corresponding lateral boreholes 260 and peripheral screw holes 360, respectively. This angle is designed such each peripheral screw 680 purchases optimal cortical bone according to the preoperative plan.

Figure 11A:
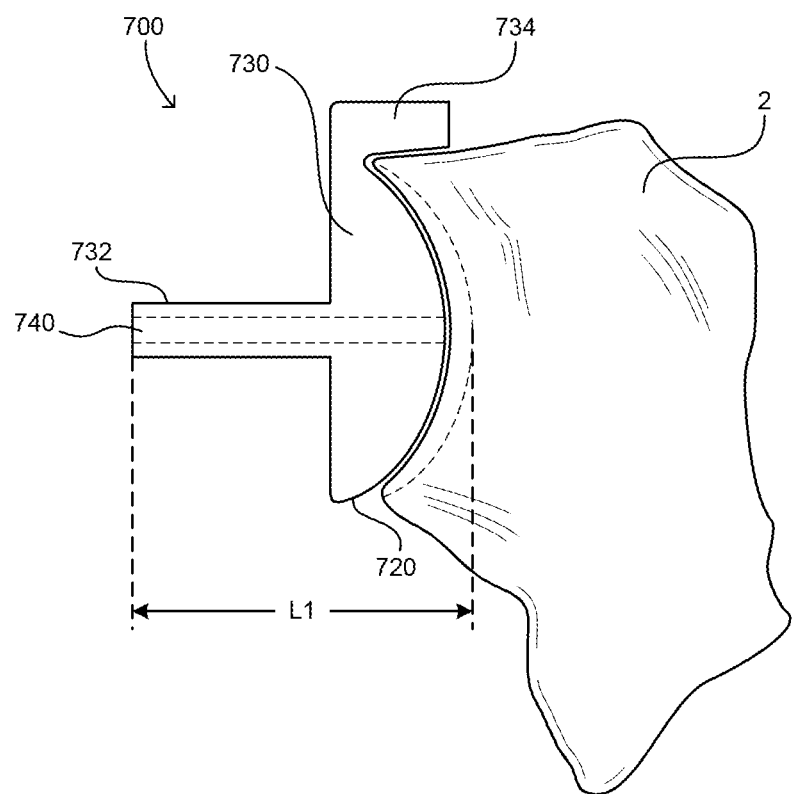
FIG. 11A is a partial cross-sectional plan view of one embodiment of a patient-specific guide engaged to native bone of a glenoid cavity and scapular bone.

FIGS. 11A-12D show a system of components for resecting a preoperatively planned depth D1 into bone. FIG. 11A shows guide 700 contacting a surface of scapular bone 2 in a preoperatively planned position. Guide 700 has a patient-specific inner contact surface 720 and a bore hole 740. Guide 700 further includes a base portion 730 and a shaft portion 732. Cannulated portion or borehole 740 extends through the base portion 730 and the shaft portion 732 and has a preoperatively planned length L1. Patient-specific inner contact surface 720 extends from base portion 730 to a flange portion 734 such that contact surface 720 contacts the glenoid cavity as well as around and adjacent the scapular rim. As described above, the contact surface 720 is shaped based on preoperative image information such that guide 700 contacts bone 2 in only one preoperatively planned position.

Figure 11B:
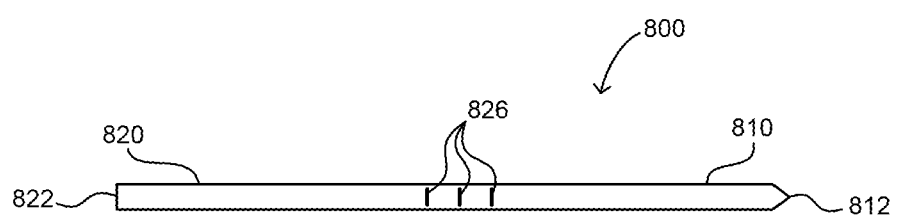
FIG. 11B is a plan view of another embodiment of a guidewire gauge or marking pin of the present invention.

FIG. 11B is one embodiment of a guidewire gauge or marking pin 800 for guiding reaming depth of a glenoid. Gauge 800 includes a first portion 810 having a first end 812 and a second portion 820 having a second end 822. Gauge 800 further includes a plurality of depth markings 826 on an outer surface of gauge 800 along a length of gauge 800.

Figure 11C:
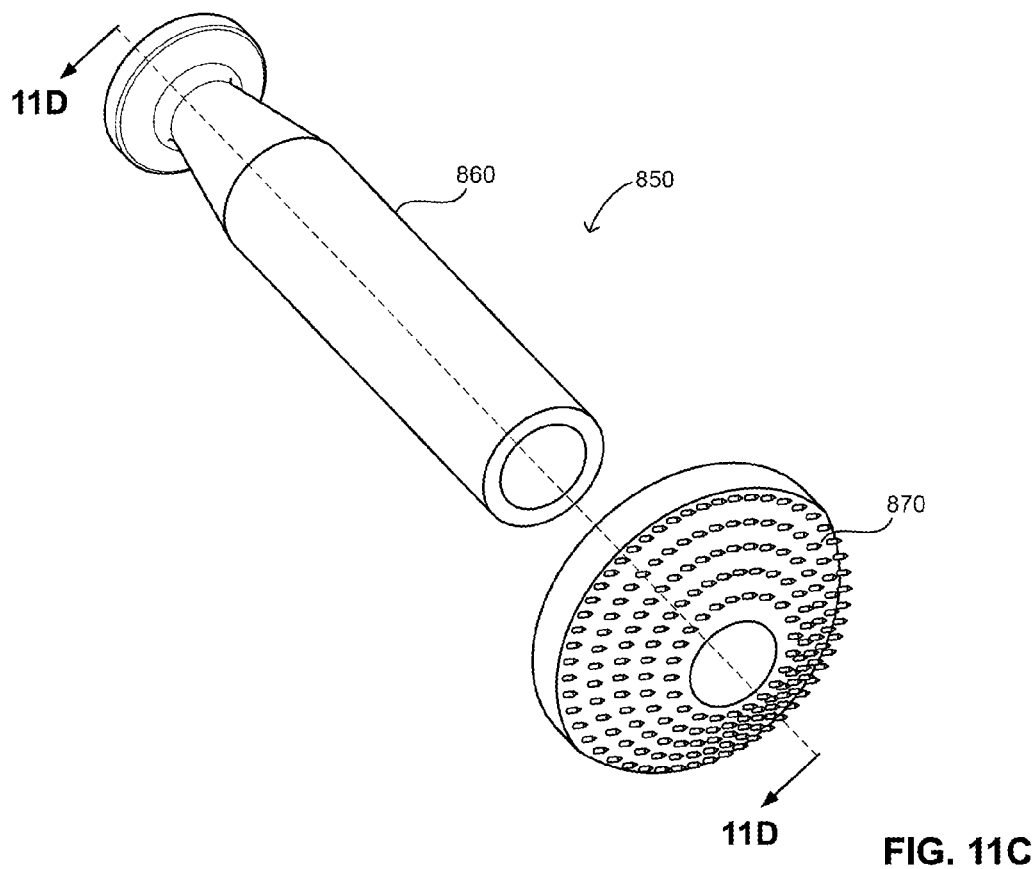
FIG. 11C is a perspective exploded view of a cannulated reamer having a shaft portion and a reamer portion.
Figure 11D:
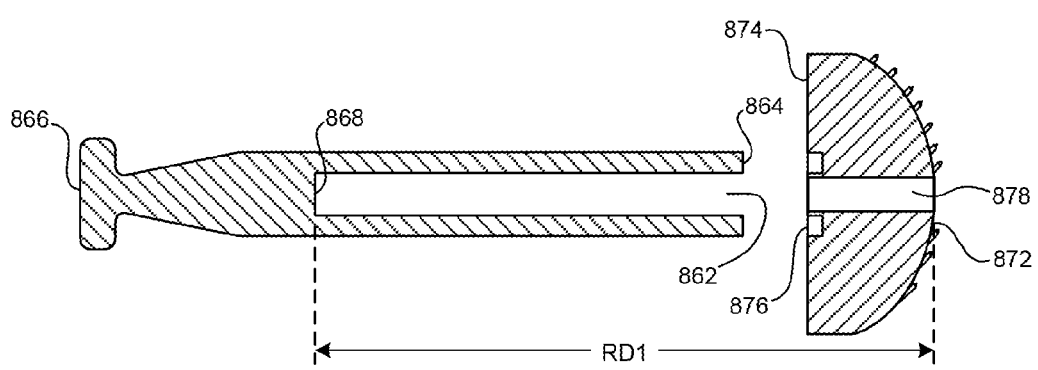
FIG. 11D is a cross-sectional view of the cannulated reamer portions shown in FIG. 11C.
Figure 12A:
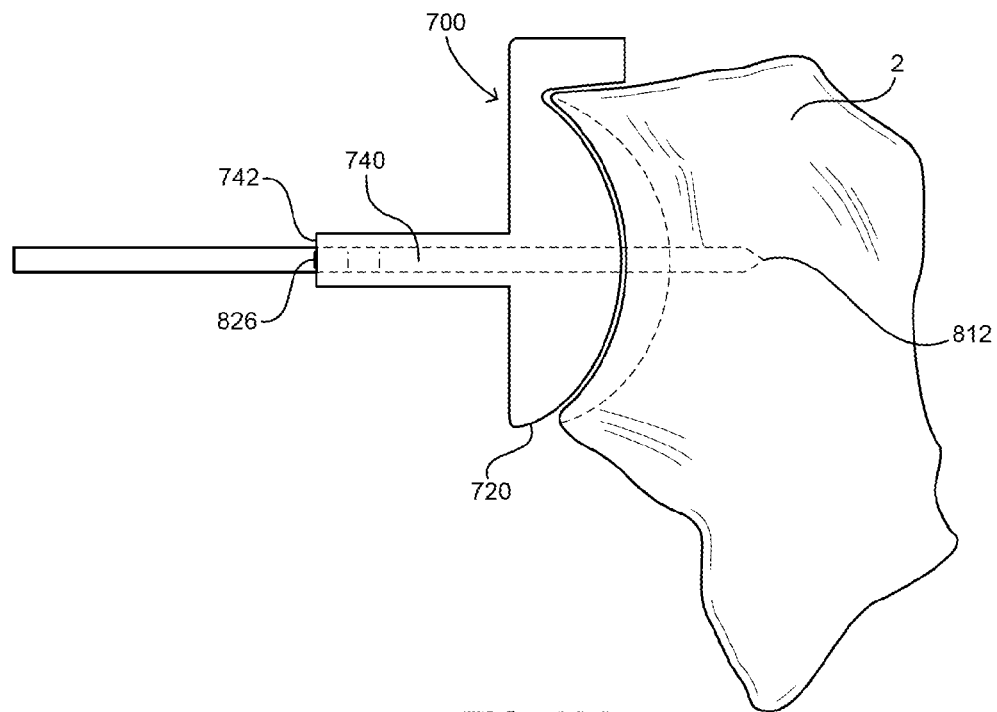
FIG. 12A is a partial cross-sectional plan view of one embodiment of the guidewire gauge shown in FIG. 11B at least partially housed within the patient-specific guide shown in FIG. 11A and engaged to native bone of the glenoid cavity and scapular bone.
Figure 12B:
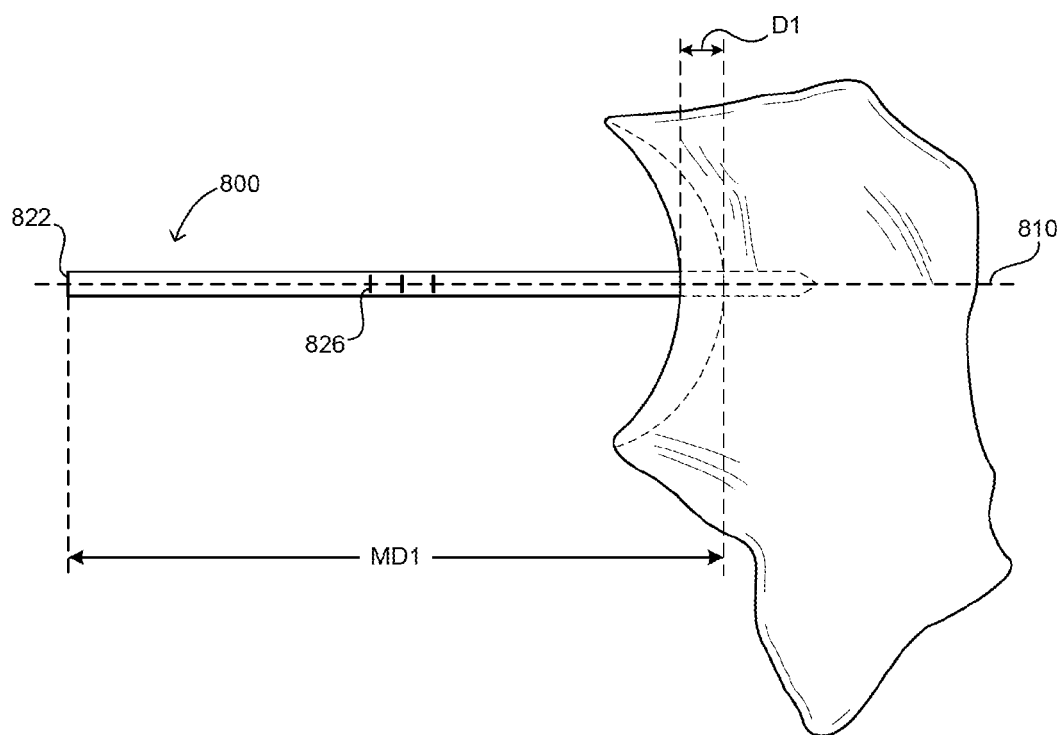
FIG. 12B is a partial cross-sectional view of the guidewire gauge shown in FIG. 12A with the patient-specific guide having been removed.
Figure 12C:
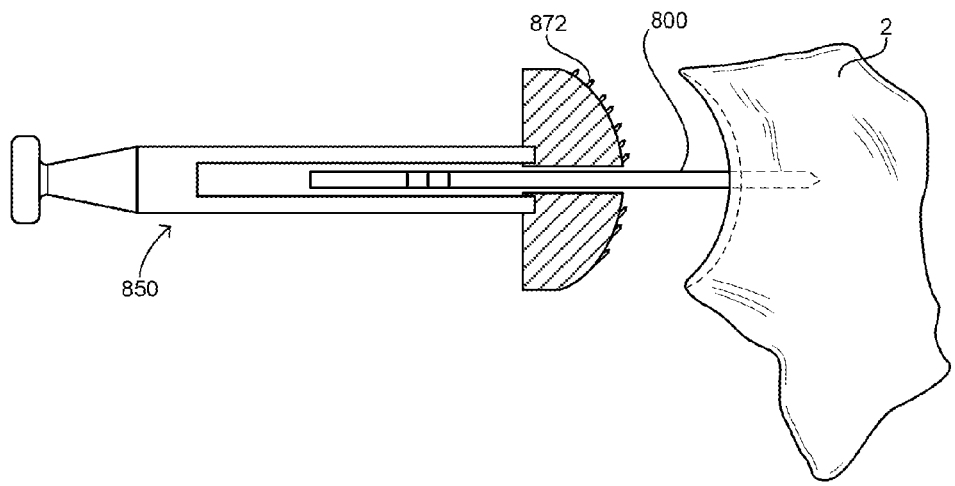
FIG. 12C is a plan view of the guidewire gauge shown in FIG. 12B at least partially housed within the cannulated reamer of FIG. 11C.

FIG. 11C is a perspective exploded view of a cannulated reamer 850 having a shaft portion 860 and a reamer portion 870. Shaft portion 860 has an internal guide portion 862 terminating at a stop surface 868, a first end portion 864 and a second end portion 866. Reamer portion 870 includes an outer reamer surface 872, a base surface 874 having a groove 876 therein, and a cannulated portion or borehole 878 extending through the outer reamer surface 872 and base surface 874. Groove 876 is preferably circular and is adapted to receive first end portion 864 of shaft portion 860 in order to couple reamer portion 870 to shaft portion 860 as shown in FIG. 12C. A linear reamer distance RD1 is defined by a distance between outer reamer surface 872 of reamer portion 870 adjacent the cannulated portion 878 thereof and the stop surface 868 of the internal guide portion 862 of the shaft portion 860.

In a method of resecting a preoperatively planned depth D1 into bone 2 each of guide 700, marking pin 800 and cannulated reamer 850 are used. Software is used to assess cortical thickness of glenoid 8 of bone 2 and a desired amount of bone that should be resected in order to achieve proper glenoid baseplate location and orientation. The desired amount of bone that will be resected during reaming is translated into reaming depth D1. The analysis of the cortical thickness sets the recommended reaming depth D1 that optimizes cortical thickness for a given baseplate curvature. This allows for maximum placement of the baseplate and inhibits over-reaming the glenoid in improper version.

In one step of the method, patient-specific inner contact surface 720 is placed against bone 2 in its preoperatively planned position. In another step, a first end 812 of marking pin 800 is inserted into cannulated portion 740 of guide 700 and into contact with the surface of bone 2. Marking pin 800 is then drilled into bone until a determined reference feature or depth marking 826 on an outer surface of marking pin 800 lies adjacent a receiving end 742 of cannulated portion 740 of guide 700 as shown in FIG. 12A. The length of cannulated portion 740 is designed in order to accurately position the marking pin 800 in bone 2 such that the cannulated reamer 850 resects a desired depth D1 into bone 2. Because the length of cannulated portion 740 is known, it can be preoperatively determined how deep marking pin 800 will be drilled into bone 2 based on the location of a particular depth marking on the outer surface of marking pin 800 that will lie adjacent the receiving end 742 of cannulated portion 740 of guide 700. Once the marking pin 800 is drilled in bone 2 a desired depth, guide 700 is removed leaving the marking pin coupled to bone 2 as shown in FIG. 12B. A linear marking distance MD1 is defined by the distance between second end 822 of marking pin 800 and a location of a desired reaming depth inside bone 2 along a longitudinal axis 810 of marking pin 800. The linear reamer distance RD1 being at least substantially the same as the linear marking distance MD1.

Figure 12D:
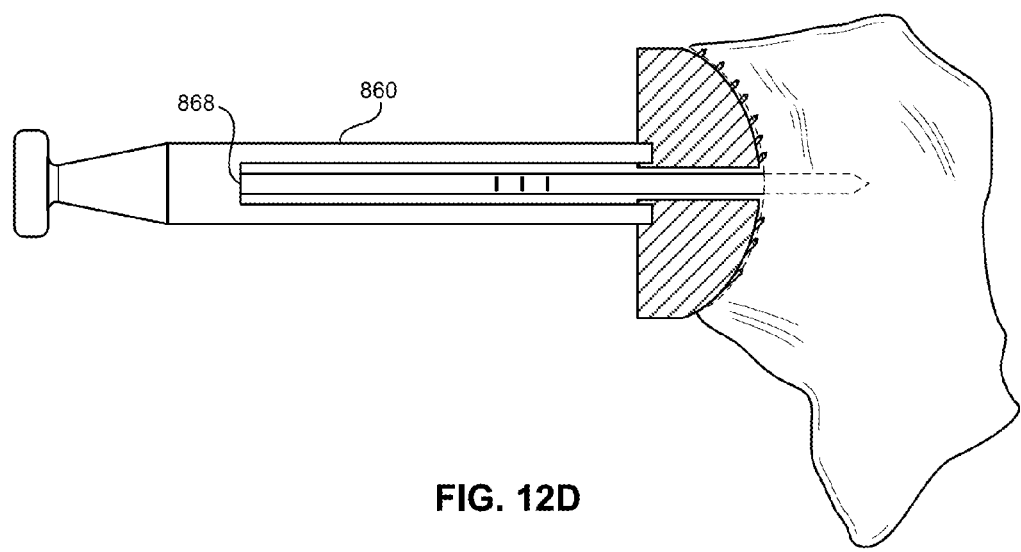
FIG. 12D is a plan view of the guidewire gauge shown in FIG. 12B fully seated within the cannulated reamer of FIG. 11C.

FIG. 12C is a plan view of marking pin or gauge 800 shown in FIG. 12B at least partially housed within cannulated reamer 850 of FIG. 11C. The advancement of cannulated reamer 850 is guided by gauge 800 until gauge 800 comes in contact with stop surface 868 such that it is fully seated within cannulated reamer 850 as shown in FIG. 12D. Contact between gauge 800 and stop surface 868 provides tactile indication that reaming is completed. Such contact may be visualized through a viewing window (not shown) in shaft portion 860 of cannulated reamer 850. Once gauge 800 is fully seated in cannulated reamer 850, the preoperatively planned depth D1 into bone 2 has been achieved. The amount of bone resected depends on the angle the gauge 800 was inserted into bone 2 and also the topography of the bone itself. Although outer reamer surface 872 has a curvature preferably substantially similar to that of a corresponding glenoid baseplate surface, the amount of bone 2 resected along the outer reamer surface 872 may not be constant based on the topography of bone itself.

Figure 13A:
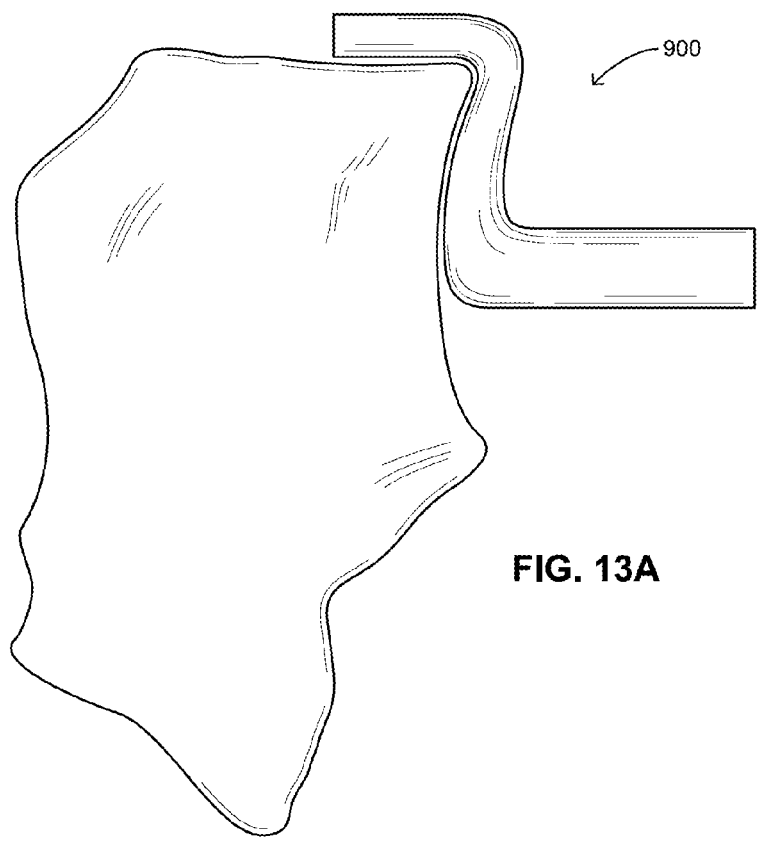
FIG. 13A is plan view of another embodiment of a patient-specific guide engaged to native bone of a glenoid cavity and scapular bone.
Figure 13B:
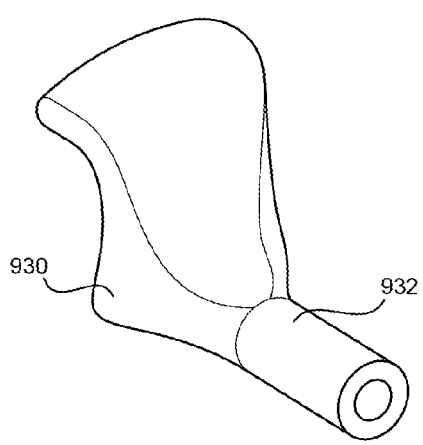
FIG. 13B is a perspective view of the patient-specific guide shown in FIG. 13A.
Figure 13C:
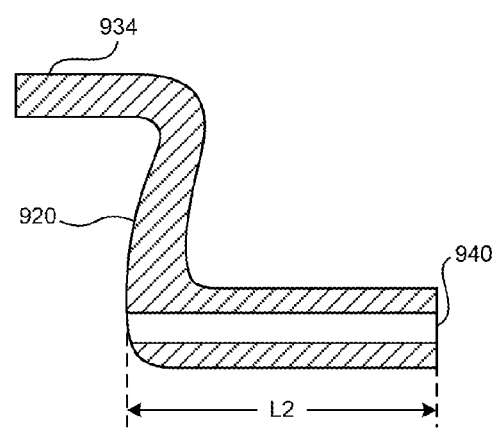
FIG. 13C is a cross-sectional plan view of the patient-specific guide shown in FIG. 13B taken along line 13B-13B.

FIG. 13A-13C show another embodiment of a patient-specific guide 900 engaged to native bone of a glenoid cavity and scapular bone. Guide 900 has a patient-specific inner contact surface 920 and a bore hole 940. Guide 900 further includes a base portion 930 and a shaft portion 932. Cannulated portion or borehole 940 extends through the base portion 930 and the shaft portion 932 and has a preoperatively planned length L2. Patient-specific inner contact surface 920 extends from base portion 930 to a flange portion 934 such that contact surface 920 contacts the glenoid cavity as well as around and adjacent the scapular rim. As described above, the contact surface 920 is shaped based on preoperative image information such that guide 900 contacts bone 2 in only one preoperatively planned position.

FIG. 13D is a plan view of cannulated portions 1040, 1140, 1240 and 1340 of four patient-specific guides 1000, 1100, 1200 and 1300 respectively each having a different lengths L3-L6. The length of these cannulated portions is designed in order to accurately position a marking pin, such as marking pin 800 into bone such that the a cannulated reamer, such as cannulated reamer 850 resects a desired depth D1 into the bone. Because the lengths of the cannulated portions is known, it can be preoperatively determined how deep marking pin 800 will be drilled into the bone based on the location of a particular depth marking on the outer surface of marking pin 800 that will lie adjacent the receiving ends 1042, 1142, 1242 and 1342 of cannulated portions 1040, 1140, 1240 and 1340 respectively.

FIG. 14A shows another embodiment of a gauge 1500 prior to being received in a cannulated portion 1440 of a patient-specific guide 1400. FIG. 14B shows gauge 1500 at least partially housed within cannulated portion 1440 of patient-specific guide 1400, the cannulated portion 1440 having a protrusion or grasping feature 1482 projecting outwardly from an inner wall surface 1480 of cannulated portion 1440. Cannulated portion 1440 of guide 1400 has a receiving end 1464 and an exiting end 1466, the internal wall surface 1480 adjacent receiving end 1464 of cannulated portion 1440 having the protrusion or grasping feature 1482 extending outwardly therefrom. The plurality of reference features 1526 in an outer surface 1528 of marking pin or gauge 1500 are indentations such that when the gauge 1500 is received in receiving end 1464 of cannulated portion 1440 of guide 1400 and translates with respect to cannulated portion 1440 until the grasping feature 1526 engages the indentation to inhibit the translation of the gauge 1500 with respect to cannulated portion 1440.

Figure 15A:
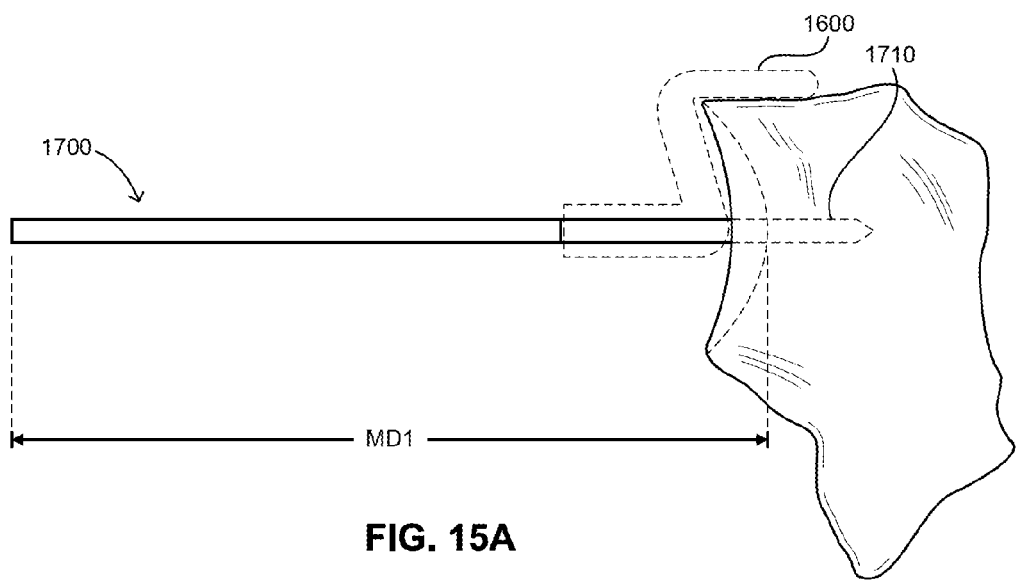
FIG. 15A is a partial cross-sectional plan view of one embodiment of a guidewire gauge with an embodiment of a patient-specific guide in phantom lines wherein a distance MD1 is measured from an end of the guidewire gauge to an end of a desired resection in the glenoid cavity.
Figure 15B:
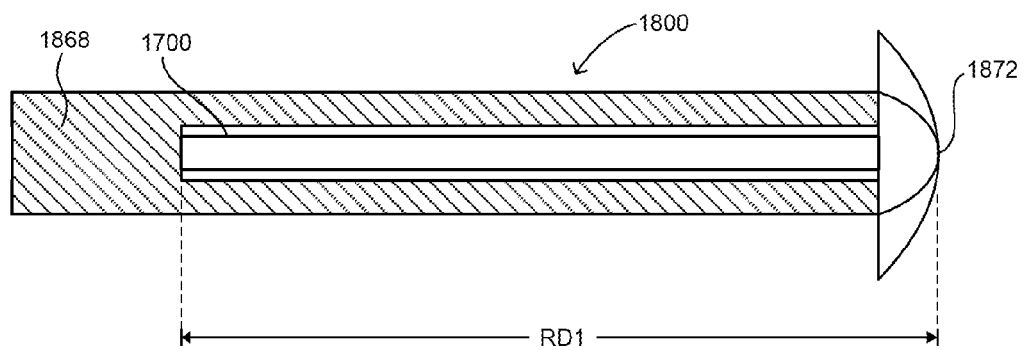
FIG. 15B is a partial cross-sectional plan view of the guidewire gauge shown in FIG. 15B fully seated within a cannulated reamer shown a distance RD1 measured from an end of the cannulation of the cannulated reamer to an apex surface of the reamer portion.

FIG. 15A shows another embodiment of a guidewire gauge 1700 with another embodiment of a patient-specific guide 1600 in phantom lines where a linear marking distance MD1 is measured from an end of gauge 1700 to a nadir point 1710 along a surface of a desired resection line in the glenoid cavity. FIG. 15B shows gauge 1700 fully seated within a cannulated reamer 1800 where a linear marking distance MD1 is measured from a stop surface 1868 at an end of the cannulation of cannulated reamer 1800 to an apex point 1872 of the reamer portion 1870 of the cannulated reamer 1800. The linear reamer distance RD1 being at least substantially the same as the linear marking distance MD1.

Figure 16:
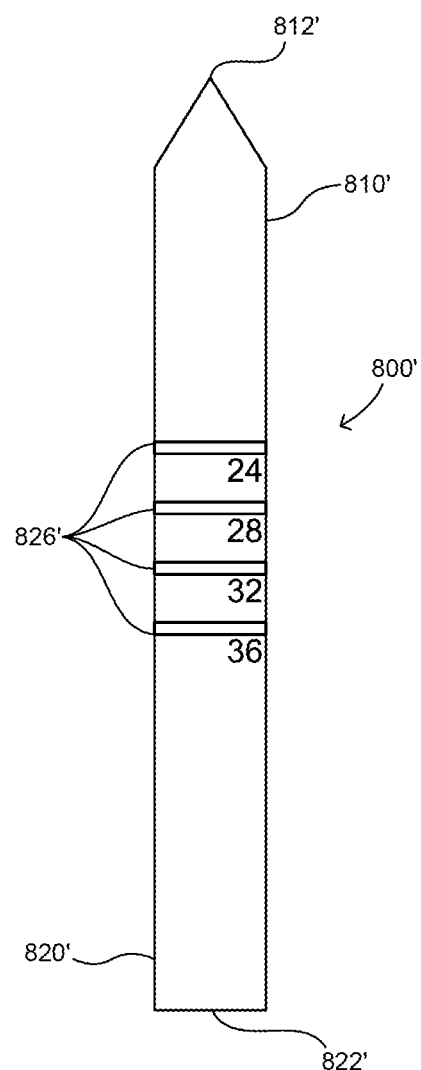
FIG. 16 is a plan view of another embodiment of a marking pin or guidewire gauge.

FIG. 16 shows another embodiment of a marking pin or guidewire gauge 800'. Gauge 800' includes a first portion 810' having a first end 812' and a second portion 820' having a second end 822'. Gauge 800' further includes a plurality of depth markings 826' on an outer surface of gauge 800' along a length of gauge 800'. The depth marking 826' are shown as measurement lines on the outer surface of gauge 800'. For example, the numerals "24," "28," "32," and "36" each refer to appropriate depth to allow proper insertion depth as well as built-in reaming depth when inserted to proper setting. These notches or lines represent appropriate setting distance given reamer depth and size of center screw that will be used to fix a glenoid baseplate to the resected glenoid cavity.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A shoulder guide for resecting a preoperatively planned depth into bone comprising:
    a body having a patient specific contact surface that contacts a surface of the bone in a preoperatively planned position, the body having an L-shaped flange portion and a first cannulated portion, the flange portion extending away from the first cannulated portion and being configured to contact a glenoid cavity and around a scapular rim; and
    a guide shaft projecting from the body, the guide shaft having a second cannulated portion aligned with the first cannulated portion of the body,
    wherein the first and second cannulated portions form a throughbore having a predefined length defined from a distal end surface of the guide shaft to an opening in the patient specific contact surface of the body, and
    wherein the preoperatively planned depth is based on the predefined length and a location of at least one reference feature of a marking pin.

2. The shoulder guide of claim 1, wherein the distal end surface of the guide shaft forms a first planar surface.

3. The shoulder guide of claim 2, wherein a distal end surface of the body forms a second planar surface.

4. The shoulder guide of claim 3, wherein a length of the guide shaft is defined about a longitudinal axis extending from the first planar surface to the second planar surface.

5. The shoulder guide of claim 1, wherein the throughbore terminates at a proximal end of the body adjacent the patient specific contact surface.

6. The shoulder guide of claim 3, wherein the second cannulated portion is defined by a linear distance between the first and second planar surfaces.

7. The shoulder guide of claim 1, wherein the guide shaft has an inner cylindrical wall.

8. The shoulder guide of claim 7, wherein the guide shaft has an outer cylindrical wall.

9. The shoulder guide of clam 8, wherein the guide shaft has a thickness defined by the inner and outer cylindrical walls.

10. The shoulder guide of claim 9, wherein a marking pin having a first end is adapted to be drilled into the bone a linear marking distance, the preoperatively planned depth being defined by a depth the marking pin is drilled into the bone.

11. A system for resecting a preoperatively planned depth into bone comprising:
   a guide having a patient specific contact surface that contacts a surface of the bone in a preoperatively planned position, the guide having a cannulated portion including a predefined length;
   a marking pin having first and second ends, the preoperatively planned depth being defined by a depth the marking pin is drilled into the bone; and
   a cannulated reamer having a shaft portion coupled to a reamer portion and defining a linear reamer distance,
   wherein the predefined length of the cannulated portion of the guide is based on a location of the at least one reference feature on the outer surface of the marking pin, and
   wherein the linear reamer distance is substantially the same as a linear marking distance defined by a linear distance between the second end of the marking pin and a preoperatively planned resection depth into the bone.

12. The system of claim 11, wherein the marking pin has at least one reference feature on an outer surface thereof, the at least one reference feature of the marking pin lying adjacent to a receiving end of the cannulated portion when the marking pin is received within the cannulated portion of the guide and the marking pin is drilled into bone the preoperatively planned resection depth.

13. The system of claim 11, wherein the shaft portion has an internal guide portion and the reamer portion includes a central aperture.

14. The system of claim 13, wherein the marking pin is adapted to be inserted through the central aperture and into the internal guide portion.

15. The system of claim 14, wherein the internal guide portion includes a stop surface.

16. The system of claim 15, wherein the linear reamer distance is defined by a distance between an outer surface of the reamer portion adjacent the central aperture thereof and the stop surface of the guide portion of the shaft portion.

17. The system of claim 16, wherein a linear resection depth is defined by the distance between the surface of the bone prior to resection and a location of the preoperatively planned resection depth inside the bone.

18. The system of claim 11, wherein the cannulated portion of the guide forms an internal wall having a receiving end and an exiting end.

19. The system claim of 18, wherein the internal wall is adjacent the receiving end of the cannulated portion having a protrusion extending outwardly therefrom.

20. The system of claim 19, wherein the at least one reference feature on the outer surface of the marking pin is an indentation such that when the marking pin is received in the receiving end of the cannulated portion of the guide and translates with respect to the cannulated portion until the protrusion engages the indentation to inhibit the translation of the marking pin with respect to the cannulated portion.

* * * * *